(12) United States Patent
Lu et al.

(10) Patent No.: US 12,174,170 B2
(45) Date of Patent: Dec. 24, 2024

(54) BIOCHIP PACKAGING STRUCTURE

(71) Applicant: Kore Semiconductor Co., Ltd., Qingdao (CN)

(72) Inventors: Hsiang-Hua Lu, New Taipei (TW); Ying-Chieh Pan, New Taipei (TW); Ching-Yu Ni, New Taipei (TW)

(73) Assignee: Kore Semiconductor Co., Ltd., Qingdao (CN)

( * ) Notice: Subject to any disclaimer, the term of this patent is extended or adjusted under 35 U.S.C. 154(b) by 536 days.

(21) Appl. No.: 16/884,414

(22) Filed: May 27, 2020

(65) Prior Publication Data

US 2021/0154666 A1    May 27, 2021

(30) Foreign Application Priority Data

Nov. 22, 2019    (CN) .......................... 201911154919.5

(51) Int. Cl.
*G01N 33/48*    (2006.01)

(52) U.S. Cl.
CPC ...... *G01N 33/48* (2013.01); *B01L 2300/0819* (2013.01); *B01L 2300/0877* (2013.01)

(58) Field of Classification Search
CPC .................. G01N 33/48; G01N 33/528; B01L 2300/0819; B01L 2300/0877; B01L 3/502715; B01L 2300/0645; B01L 3/502707; B81B 2201/0214; B81B 2201/058; B81B 7/0061; B81B 2207/096; B81C 2203/0154
See application file for complete search history.

(56) References Cited

U.S. PATENT DOCUMENTS

| | | | |
|---|---|---|---|
| 2010/0230803 A1* | 9/2010 | Chien | B81C 1/00301 257/693 |
| 2014/0084458 A1* | 3/2014 | Huang | H01L 23/49827 257/737 |
| 2016/0211204 A1* | 7/2016 | Hu | H01L 23/49827 |
| 2016/0212852 A1* | 7/2016 | Hu | H01L 24/24 |

FOREIGN PATENT DOCUMENTS

| | | |
|---|---|---|
| CN | 107502534 A | 12/2017 |
| EP | 0268648 B1 * | 4/1991 |
| TW | I637834 B * | 10/2018 |
| TW | I673834 B | 10/2019 |

* cited by examiner

*Primary Examiner* — Samuel P Siefke
*Assistant Examiner* — Henry H Nguyen
(74) *Attorney, Agent, or Firm* — ScienBiziP, P.C.

(57) ABSTRACT

A biochip packaging structure includes a chip packaging layer, a redistribution layer, and a microfluidic channel. The chip packaging layer includes a resin layer including a biochip and a conductive pillar located on each of two sides of the biochip. The biochip includes a first surface flush with and exposed out of a side of the resin layer. A first end of the conductive pillar is flush with a side of the resin layer opposite the biochip. A second end of the conductive pillar is flush with the first surface of the biochip. The redistribution layer includes a metal winding electrically coupled to the biochip and the adjacent conductive pillar. The metal winding includes a first winding portion coupled to the biochip and a second winding portion coupled between the first winding portion and the conductive pillar. The second winding portion is parallel to the first surface.

6 Claims, 1 Drawing Sheet

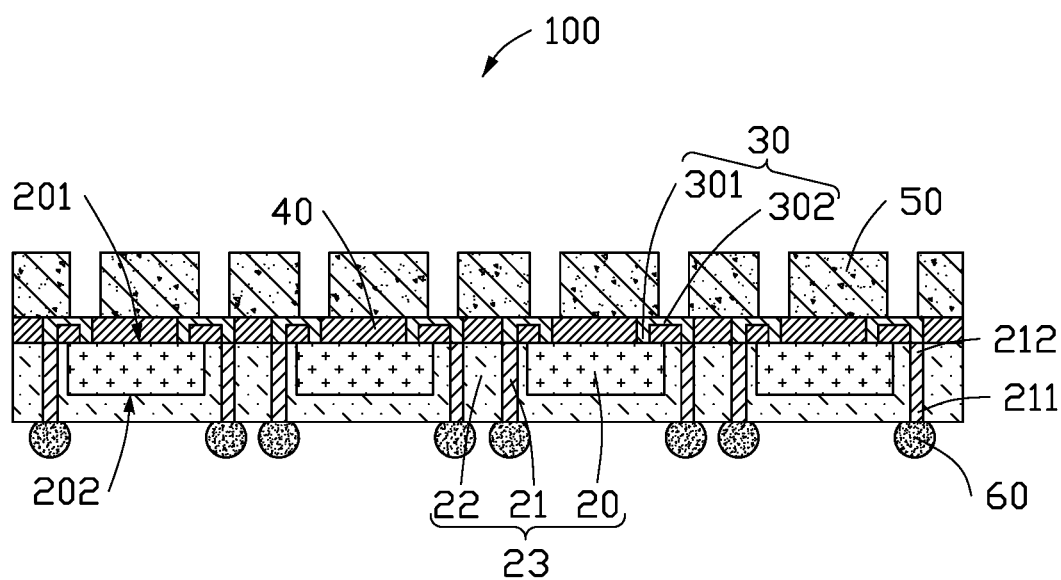

BIOCHIP PACKAGING STRUCTURE

FIELD

The subject matter herein generally relates to biochips, and more particularly to a biochip packaging structure.

BACKGROUND

Biochips are used for rapid detection of DNA, RNA, peptides, proteins, and other biological components on a surface of the biochip. The biochips are widely used in the biomedical field to rapidly obtain disease detection results.

At present, the biochip is generally connected to a substrate by wire bonding, but this causes the surface of the biochip to be uneven. After a microfluidic channel is affixed to the surface of the biochip, liquid leakage may occur due to unevenness of the microfluidic channel on the surface of the biochip, thereby affecting the detection results.

BRIEF DESCRIPTION OF THE DRAWINGS

Implementations of the present disclosure will now be described, by way of embodiments, with reference to the attached figures.

FIG. 1 is a cross-sectional view of an embodiment of a biochip packaging structure.

DETAILED DESCRIPTION

It will be appreciated that for simplicity and clarity of illustration, where appropriate, reference numerals have been repeated among the different figures to indicate corresponding or analogous elements. Additionally, numerous specific details are set forth in order to provide a thorough understanding of the embodiments described herein. However, it will be understood by those of ordinary skill in the art that the embodiments described herein can be practiced without these specific details. In other instances, methods, procedures and components have not been described in detail so as not to obscure the related relevant feature being described. The drawings are not necessarily to scale and the proportions of certain parts may be exaggerated to better illustrate details and features. The description is not to be considered as limiting the scope of the embodiments described herein.

Several definitions that apply throughout this disclosure will now be presented.

The term "coupled" is defined as connected, whether directly or indirectly through intervening components, and is not necessarily limited to physical connections. The connection can be such that the objects are permanently connected or releasably connected. The term "substantially" is defined to be essentially conforming to the particular dimension, shape, or other word that "substantially" modifies, such that the component need not be exact. For example, "substantially cylindrical" means that the object resembles a cylinder, but can have one or more deviations from a true cylinder. The term "comprising" means "including, but not necessarily limited to"; it specifically indicates open-ended inclusion or membership in a so-described combination, group, series and the like.

FIG. 1 shows an embodiment of a biochip packaging structure 100. The biochip packaging structure 100 includes a chip packaging layer 23, a redistribution layer 40, a microfluidic channel 50, and at least one solder ball 60.

The chip packaging layer 23 includes a resin layer 22. The resin layer 22 includes at least one biochip 20 and a conductive pillar 21 located on each of two sides of each biochip 20. In one embodiment, a material of the resin layer 22 is polyimide.

The biochips 20 are arranged at intervals in the resin layer 22. The biochip 20 includes a first surface 201 and a second surface 202 opposite to the first surface 201. The first surface 201 is flush with a side of the resin layer 22 and exposed from the resin layer 22. The first surface 201 is provided with a sensing area (not shown), and the sensing area is also exposed from the resin layer 22. The biochip 20 can be applied to various medical and biochemical tests, such as obtaining gene sequences, analyzing protein composition, checking pH values, and the like, so as to realize detection of biological body fluids.

The conductive pillar 21 includes a first end 211 and a second end 212 opposite to the first end 211. The first end 211 is flush with a side of the resin layer 22 opposite the first surface 201. The second end 212 is flush with the side of the resin layer 22 flush with the biochip 20. In one embodiment, the conductive pillar 21 is arranged perpendicular to the first surface 201 and the second surface 202. A material of the conductive pillar 21 is a metal with high conductivity such as copper, silver, gold, or tungsten. In one embodiment, the material of the conductive pillar 21 is metallic copper.

The redistribution layer 40 is formed on the chip packaging layer 23. At least one metal winding 30 is located in the redistribution layer 40. Each of the metal windings 30 is electrically connected to the sensing region of each of the biochips 20 and the conductive pillar located adjacent to the metal winding 30. Each of the metal windings 30 includes a first winding portion 301 connected to the sensing area, and a second winding portion 302 connected between the first winding portion 301 and the conductive pillar 21. The first winding portion 301 may be substantially perpendicular to the first surface 201. The second winding portion 302 may be substantially parallel to the first surface 201. Therefore, a surface of the redistribution layer 40 is substantially flat.

A material of the metal winding 30 is a metal having high conductivity, such as copper, silver, gold, or tungsten. In one embodiment, the material of the metal winding 30 is metal copper.

The microfluidic channel 50 is formed on the redistribution layer 40 and corresponds to the sensing area of the biochip 20. In one embodiment, the microfluidic channel 50 is a thin film. The microfluidic channel 50 can be used for mixing, transmission, and separation of biological fluids. Through the use of the biochip 20, the microfluidic channel 50 can reduce error of manual operation experiments, reduce energy consumption and the required amount of biological fluids, and save manpower and time.

The metal winding 30 ensures the flatness of the redistribution layer 40, so that the microfluidic channel 50 can be integrated on the surface of the redistribution layer 40. The related art uses a wire bonding method, which makes the surface of the redistribution wiring layer 40 uneven, so that the microfluidic channel 50 will leak when the biological liquid is injected due to the unevenness of the redistribution wiring layer 40.

Each of the solder balls 60 is connected to the second end 212 of a respective one of the conductive pillars 21. The solder ball 60 is used to connect with an external device (not shown), so as to realize signal transmission between the biochip package structure 100 and the external device.

In use, a biological fluid is injected into the microfluidic channel 50, and the biological fluid is detected by the sensing area of the biochip 20. A detection result of the biochip 20 is transmitted to the external device through the redistribution layer 40, the conductive pillars 21, and the solder balls 60 for analysis.

In the biochip packaging structure, by using the metal winding 30 between the sensing area of each of the biochips 20 and the adjacent conductive pillar 21, the metal winding 30 is arranged parallel to the surface of the biochip 20, so that the redistribution layer 40 and the microfluidic channel 50 are flat, thereby preventing the microfluidic channel 50 on the surface of the biochip 20 from leaking when a biological fluid is injected, and thereby improving a detection result. Furthermore, the biochip packaging structure 100 does not use a substrate, which reduces a thickness of the biochip packaging structure 100. In addition, the microfluidic channel 50 is a thin film, which further reduces the thickness of the biochip packaging structure 100 and further expands an application range of the biochip packaging structure 100.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in matters of shape, size and arrangement of the parts within the principles of the present disclosure up to, and including, the full extent established by the broad general meaning of the terms used in the claims.

What is claimed is:

1. A biochip packaging structure comprising:
a chip packaging layer comprising a resin layer, the resin layer comprising at least one biochip and a conductive pillar located on each of two sides of each of the at least one biochip, the at least one biochip comprising a first surface flush with and exposed out of a side of the resin layer, the conductive pillar comprising a first end and a second end, wherein the second end is opposite to the first end, wherein the first end is flush with a side of the resin layer opposite the biochip, the second end is flush with the first surface of the biochip;
a redistribution layer formed on the chip packaging layer, at least one metal winding is located in the redistribution layer which surrounds and is separate from the at least one metal winding, each of the at least one metal windings is electrically coupled to one of the at least one biochips and the adjacent conductive pillar, each of the at least one metal windings comprises a first winding portion coupled to the biochip and a second winding portion coupled between the first winding portion and the conductive pillar, the first winding portion is perpendicular to the first surface of the at least one biochip and a lower end of the first winding portion is flush with the resin layer, the second winding portion is parallel to the first surface, spaced away from the biochip by the redistribution layer, and exposed out of a side of the redistribution layer opposite to the first surface, and an entire surface of the redistribution layer facing away from the chip packaging layer is continuously flat; and
a microfluidic channel directly formed within a thin film and on the redistribution layer, wherein the redistribution layer is exposed from the thin film through the microfluidic channel.

2. The biochip packaging structure of claim 1, wherein:
the microfluidic channel corresponds to the first surface of the biochip.

3. The biochip packaging structure of claim 1, wherein:
the chip packaging layer comprises at least one solder ball coupled to the first end of at least one of the conductive pillars.

4. A biochip packaging structure comprising:
a chip packaging layer comprising a resin layer, the resin layer comprising at least one biochip and a conductive pillar located on each of two sides of the at least one biochip, the at least one biochip comprising a first surface flush with and exposed out of a side of the resin layer;
a redistribution layer formed on the chip packaging layer and electrically coupled to the at least one biochip and the conductive pillars, at least one metal winding is located in the redistribution layer which surrounds and is separate from the at least one metal winding, each of the at least one metal winding is electrically coupled to one of the at least one biochips and the adjacent conductive pillar, each of at least one the metal windings comprises a first winding portion coupled to the biochip and a second winding portion coupled between the first winding portion and the conductive pillar, the first winding portion is perpendicular to the first surface of the at least one biochip and a lower end of the first winding portion is flush with the resin layer, the second winding portion is parallel to the first surface, spaced away from the biochip by the redistribution layer, and exposed out of a side of the redistribution layer opposite to the first surface, and an entire surface of the redistribution layer facing away from the chip packaging layer is continuously flat;
a microfluidic channel directly formed within a thin film and on the redistribution layer, wherein the redistribution layer is exposed from the thin film through the microfluidic channel; and
at least one solder ball coupled to a corresponding one of the conductive pillars;
wherein the chip packaging layer and the at least one biochip are flush with the redistribution layer; and
wherein the microfluidic channel is flush with the redistribution layer.

5. The biochip packaging structure of claim 4, wherein:
the chip packaging layer further comprises a resin layer;
the at least one biochip and the conductive pillars are located in the resin layer;
the biochip comprises a first surface flush with and exposed out of a side of the resin layer;
the conductive pillar comprises a first end and a second end opposite to the first end, the first end flush with a side of the resin layer opposite to the biochip, the second end flush with the first surface of the biochip.

6. The biochip packaging structure of claim 4, wherein:
the microfluidic channel corresponds to the first surface of the biochip.

* * * * *